United States Patent [19]
Smith et al.

[11] Patent Number: 5,916,029
[45] Date of Patent: Jun. 29, 1999

[54] PROCESS FOR PRODUCING SEEDS COATED WITH A MICROBIAL COMPOSITION

[75] Inventors: R. Stewart Smith, Whitefish Bay; Robert M. Osburn, Thiensville, both of Wis.

[73] Assignee: LiphaTech, Inc., Milwaukee, Wis.

[21] Appl. No.: 08/670,450

[22] Filed: Jun. 26, 1996

[51] Int. Cl.⁶ .............................. A01C 1/06; A01C 21/00; A01C 1/00; A01B 79/00; A01N 63/00; C12N 1/20

[52] U.S. Cl. .............................. 47/57.6; 47/58; 424/93.4; 424/93.46; 424/93.47; 435/252.2; 435/252.4; 435/252.5; 435/253.3

[58] Field of Search ...................... 47/57.6, 58; 424/93.4, 424/93.46, 93.47; 435/252.2, 252.4, 252.5, 253.3

[56] References Cited

U.S. PATENT DOCUMENTS

| | | | |
|---|---|---|---|
| Re. 34,670 | 7/1994 | Williams et al. | 71/7 |
| 3,168,796 | 2/1965 | Scott et al. | 47/1 |
| 3,808,740 | 5/1974 | Porter et al. | 47/58 |
| 4,136,486 | 1/1979 | Franklin, Jr. et al. | 47/58 |
| 4,149,869 | 4/1979 | Lloyd | 71/7 |
| 4,251,952 | 2/1981 | Porter et al. | 47/57.6 |
| 4,367,609 | 1/1983 | Lloyd | 47/57.6 |
| 4,755,468 | 7/1988 | Jung et al. | 435/178 |
| 4,798,723 | 1/1989 | Dart et al. | 424/93 |
| 4,818,696 | 4/1989 | Appelbaum et al. | 435/172.3 |
| 4,849,005 | 7/1989 | Williams et al. | 71/7 |
| 4,877,738 | 10/1989 | Handelsman et al. | 435/252.5 |
| 4,878,936 | 11/1989 | Handelsman et al. | 71/7 |
| 5,026,417 | 6/1991 | Kucey | 71/35 |
| 5,041,290 | 8/1991 | Gindrat et al. | 424/93 |
| 5,049,379 | 9/1991 | Handelsman et al. | 424/115 |
| 5,106,648 | 4/1992 | Williams | 427/3 |
| 5,113,619 | 5/1992 | Leps et al. | 47/57.6 |
| 5,229,114 | 7/1993 | Cregan et al. | 424/93 |
| 5,229,291 | 7/1993 | Nielsen et al. | 435/252.2 |
| 5,264,210 | 11/1993 | Novitski et al. | 424/93 |
| 5,292,507 | 3/1994 | Charley | 424/93 |
| 5,300,127 | 4/1994 | Williams | 47/57.6 |
| 5,415,672 | 5/1995 | Fahey et al. | 47/57.6 |
| 5,427,785 | 6/1995 | Ronson et al. | 424/93.2 |
| 5,484,464 | 1/1996 | Gleddie et al. | 47/57.6 |
| 5,697,186 | 12/1997 | Neyra et al. | 47/57.6 |

FOREIGN PATENT DOCUMENTS

| | | | |
|---|---|---|---|
| 0192342A2 | 8/1986 | European Pat. Off. | A01N 63/02 |
| 0203708A1 | 12/1986 | European Pat. Off. | C12N 1/04 |
| 0226394A2 | 6/1987 | European Pat. Off. | A01N 63/00 |
| 0286351A2 | 10/1988 | European Pat. Off. | C05F 11/08 |
| 0314439A2 | 5/1989 | European Pat. Off. | C12N 1/04 |
| WO90/15136 | 12/1990 | United Kingdom | C12N 11/14 |
| WO92/08355 | 5/1992 | WIPO | A01N 63/00 |

OTHER PUBLICATIONS

1992 Article from Colorcon regarding seed coating.
Article titled "Welcome to the World of Film Coating".
May 1989 NFT Highlights article titled "NFT Gums: Ancient and Modern Commercial Products"—by Dr. D.M.W. Anderson.
Indonesian Journal of Crop Science (1986, vol. 2, No. 1, pp. 17–24) article "Gum arabic as adhesive enhances nodulation in white clover (Trifolium repens) inoculated with Rhizobium trifolii"—by Y. Taryo–Adhiwiganda.
A Wiley–Interscience Publication "A Treatise on Dinitrogen Fixation (Section IV: Agronomy and Ecology)—Application of Legume Seed Inoculants" by J. Brockwell 277+278+286.
Advances in Agronomy, vol. 42 "Seed Coatings and Treatments and Their Effects on Plant Establishment"—article by James M. Scott (43–82) 1989.
Australian Journal of Agricultural Research (vol. 13, No. 4, pp. 638–649, Jul. 1962 "Studies on Seed Pelleting as an Aid to Legume Seed Inoculation"—article by J. Brookwell.
Rhizobium Newsletter (vol. 7, No. 2—Aug., 1962) (127+128).
"Effect of Suspending Agent and Temperature on Survival of Rhizobium in Fertilizer"—article by R.J. Kremer, J. Polo, and H.L. Peterson, Soil Sci. Soc. Am. J. vol. 46 1982 (539–542).
Adhesive Increases Inoculation Efficiency in White Clover—article by J.A. Waggoner, G.W. Ever, and R.W. Weaver (375–377) Agr. J. vol. 71 Mar. Apr. 1979.
Applied and Environmental Microbiology (Jul. 1985, pp. 108–114) "Survival of Bacterial and Fungi in Relation to Water Activity and the Solvent Properties of Water in Biopolymer Gels"—article by J. Mugnier and G. Jung.
Journal of Applied Bacteriology 1993, 74, pp. 340–344 "Production and survival during storage of spray–dried Bradyrhizobium japonicum cell concentrates" Mary et al.
Reprinted from Symbiotic nitrogen fixation in plants, edited by P.S. Nutman, International Biological Programme, vol. 7. of Cambridge University Press, 1975, "Methods of inoculating seeds and their effect on survival of rhizobia" J. C. Burton; 175–189.
Persistence of Rhizobium Japonicum on the Soybean Seed Coat Under Controlled Temperature and Humidity, Applied and Environmental Microbiology, vol. 35, 1978, pp. 94–96; F. Davidson and H.W. Reuszer.

Primary Examiner—David T. Fox
Assistant Examiner—Kent L. Bell
Attorney, Agent, or Firm—Foley & Lardner

[57] ABSTRACT

A process for liquid application of a dry microbial preparation to seeds is described wherein superior survival is obtained upon drying of the preparation on the seeds. The process for coating seeds with dry, dormant microorganisms according to the invention includes an initial step of forming the dry, dormant microorganisms. Seeds are then coated with a composition comprising the dry, dormant microorganisms, water, and an additive effective for enhancing survival of the microorganisms during exposure to the water used in the coating and subsequent drying process.

17 Claims, 1 Drawing Sheet

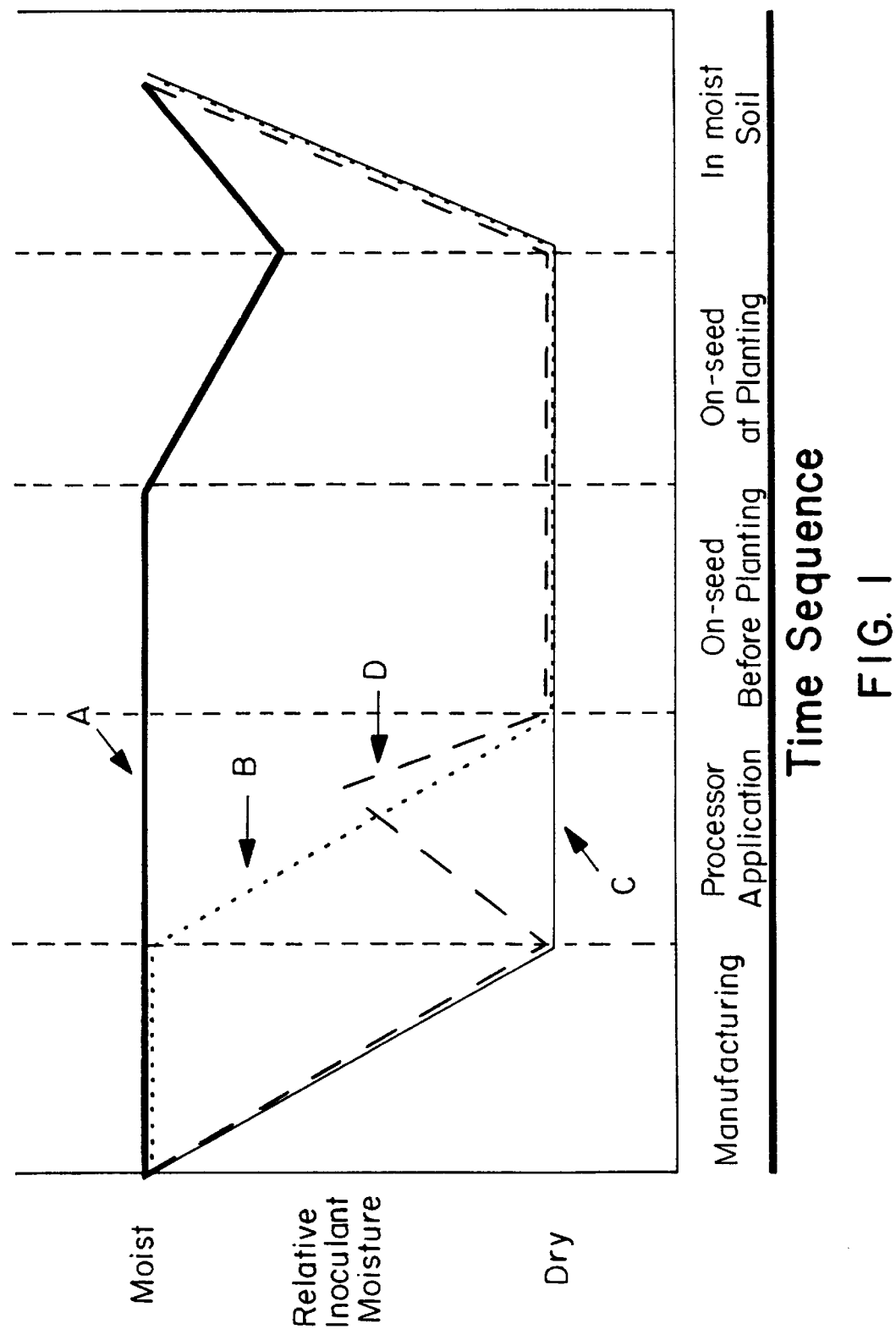

PROCESS FOR PRODUCING SEEDS COATED WITH A MICROBIAL COMPOSITION

TECHNICAL FIELD

This invention relates to an improved process for coating seeds with beneficial microorganisms such as agricultural inoculants.

BACKGROUND OF THE INVENTION

Leguminous plants fix nitrogen from the air and convert it to organic nitrogenous compounds used by the plant for protein synthesis. Nitrogen fixation in leguminous plants is possible because of the symbiotic relationship with bacteria of the genus Rhizobium and Bradyrhizobium, which forms nodules on the roots of legumes. Different species of rhizobia cause nodulation in specific legume genera. Maximum symbiotic nitrogen fixation occurs when plant and bacteria are properly matched, and when nodule formation is maximized. *Bradyrhizobium japonicum* is associated with (nodulates) soybeans, *Rhizobium leguminosarum* biovar *trifolii* with clovers, *R. meliloti* with alfalfa and sweetclovers, *R. leguminosarum* biovar *viceae* with peas and vetches, and *R. leguminosarum* biovar *phaseoli* with garden variety beans.

It is common practice to inoculate leguminous plants with rhizobia to aid nodule formation. Inoculation can be accomplished by pre-inoculating seeds, or either inoculating seeds, or placing inoculant in-furrow at planting time. Previous methods of producing an inoculant have included mixing an active, living rhizobial culture with a carrier such as humus or peat. The moist carrier maintains the bacteria in a living state.

An early method of preparing inoculants was by converting the bacteria to a dormant state. U.S. Pat. No. 3,168,796 to Scott, et al describes a method of preparing an inoculant including a step of freeze-drying. This process must be done rapidly to prevent cell rupture. The dried, ground bacteria are mixed with a powdered carrier such as kaolin or montmorillonite. Freeze-drying gives a high initial recovery of bacteria, but the inoculant does not remain stable for long storage periods.

Another method of preparing a dry, dormant inoculant is cited in PCT Published Application No. 92/08355, published May 29, 1992. The described process produces a dry, dormant bacterial composition wherein the water content is less than 5% by weight and at least $10^9$ viable bacteria per gram of the composition. The carrier is a clay mixture of montmorillonite and kaolinite which has an essentially neutral pH. Such a dry, dormant bacterial composition is available commercially under the trademark Nitragin Gold.

Biocidal compositions containing bacteria or fungi which combat insects, fungi or the like may also be prepared using the slow drying process described in the foregoing European patent publication. Interest in dry, dormant bacterial products has increased due to recent interest in biological pesticides as an ecological alternative to conventional pesticides.

Seed coating is a popular method for applying bacterial inoculants and other beneficial bacteria such as biopesticides to the target plants, particularly for alfalfa seeds. Several methods may be used to make coated alfalfa seeds, including dusting, pelleting, and film coating. Dusting of alfalfa seeds with a dry, dormant inoculant containing *R. meliloti* gives rise to a product which has an excellent shelf life, but the dust is not completely adhered to the seed, resulting in release of loose dust to the surrounding atmosphere whenever the coated seeds are handled in the open.

Film coated seeds have the advantage of not releasing dust. However, known film coating processes incorporate water in the process. Bacteria from a moist product, or which are rehydrated during the coating process, have poor viability upon subsequent drying.

A need persists for a method of preparing a coated seed wherein the bacteria in the coating have been preconditioned for survival after temporary rehydration. The adverse effects of temporary rehydration on previously dried, dormant bacteria are well known.

SUMMARY OF THE INVENTION

The present invention provides a process for liquid application of a dry microbial preparation to seeds such that superior survival is obtained upon drying of the preparation on the seeds. Such a process for coating seeds with a composition containing dry, dormant microorganisms includes an initial step of forming the dry, dormant microorganisms. The seeds are then coated with a coating composition comprising the dry, dormant microorganisms, water, and an additive effective for enhancing survival of the microorganisms during exposure to the water used in the coating process. The coated seeds are then dried. The coating and drying steps are conducted under conditions effective to enhance survival of the microorganisms when the dry, dormant microorganisms on the coated seeds are rehydrated.

The additive for enhancing survival upon drying on seeds is most effectively a carbohydrate. Suitable microorganisms include rhizobia of a species and in an amount effective to promote nitrogen fixation in a plant growing from the coated seed, and microorganisms used in an amount effective to have a plant-growth promoting/pesticidal effect on the plant that germinates from the seed. This process also allows the addition of a microbial agent plus additional beneficial additives in a continuous seed treating process. Coated seeds made according to this process have a survival rate and shelf life comparable to dusted seeds but lack the disadvantages associated with dusted seeds.

According to one aspect of the invention, a process for coating seeds with a film containing dry, dormant bacteria includes the steps of: forming dry, dormant bacteria, comprising rhizobia of a species and in an amount effective to promote nitrogen fixation in a plant growing from the coated seed, combining the bacteria with particles of a carrier such as clay to form a dry solid preparation, mixing the dry solid preparation with a solution comprising water and a carbohydrate in an amount effective for enhancing survival of the bacteria during exposure to the water to form a film forming composition, then film coating the seeds with the film forming composition, and then drying the coated seeds. The mixing, film coating and drying steps are conducted so that the dry, dormant bacteria become moistened for a sufficient time to form the film coated seeds and are returned to a dry state within a total water exposure period of no more than about 12 hours. These and other aspects of the invention are further described in the detailed description that follows.

BRIEF DESCRIPTION OF THE DRAWING

FIG. 1. The drawing is a diagram plotting relative moisture level versus time for a conventional process for making a liquid or peat-based inoculant composition (bold line—A), a conventional pelleting or slurry coating process for making an inoculant composition (dotted line—B), a conventional coating process using a dry clay preinoculant (solid line—C) and a process according to the present invention (dashed line—D).

DETAILED DESCRIPTION OF THE INVENTION

The process of the invention is carried out using microorganisms that have been dehydrated to a dormant state by any known, commercially acceptable method, such as freeze-drying, spray-drying or air-drying. A dry, dormant microorganism for purposes of the invention refers to bacteria and fungi, preferably non-endospore forming microorganisms that are capable of assuming a dry, dormant state. The invention is applicable to microbial preparations, including rhizobia and plant growth promoting and pesticidal bacteria and fungi such as Pseudomonas, Burkholdaria, Serratia, Enterobacter, Azospirillum, Trichoderma, and Gliocladium. Bacteria for use in an inoculant composition according to the invention are often a strain of the genus Rhizobium and Bradyrhizobium that nodulates one or more host plant species. Preferred species include *R. meliloti, R. leguminosarum* biovar *trifolii, R. leguminosarum* biovar *viceae, R. leguminosarum* biovar *phaseoli,* and *B. japonicum.*

Plant growth-promoting or pesticidal bacterial or fungal species useful in the present invention may have pesticidal or other properties. A number of species of this kind are known, including *Pseudomonas putida* having activity against Pythium useful in protecting dry bean and having plant growth promotion capability, and *Bacillus cereus.* One such strain known as ATCC 53522 (or UW85) is described in Handlesman et al. U.S. Pat. Nos. 4,877,738, 4,878,936, and 5,049,379, the contents of which are incorporated by reference herein. A dry, dormant inoculant bacteria such as *R. meliloti* and a dry, dormant biocidal bacteria such as ATCC 53522 may be combined and applied in a single coating in order to provide a combination product wherein the seed has enhanced nodulation and pest resistance.

A preferred method for preparing the bacteria or other suitable microbes for use in the invention is the slow drying process described in Kosanke et al. PCT Published Application No. 92/08355, May 29, 1992, and U.S. patent application Ser. No. 07/612,395, filed Nov. 13, 1990, the contents of which are incorporated by reference herein. The described process produces a dry, dormant bacterial composition wherein the water content is less than 5% by weight, preferably less than 4% by weight, with at least $10^9$ viable bacteria per gram of the composition. The carrier is a clay mixture of montmorillonite and kaolinite which has an essentially neutral pH. Such a dry, dormant bacterial composition is available commercially under the trademark Nitragin Gold.

More generally, in accordance with the foregoing preferred method, the step of forming a dry, dormant bacteria is preferably carried out by first culturing (fermenting) a species of bacteria in a growth medium to form a culture. The bacteria may be grown in a growth medium within a conventional fermentor. The culture containing the bacteria plus the growth medium is then mixed with an inert powdered carrier such as clay. The optional carrier for use in the seed coating may comprise any particulate carrier commonly used to prepare agricultural inoculants, such as clay, peat, charcoal, vermiculite, perlite or combinations thereof. The resulting mixture is incubated for 1–5 days at room temperature with no dehumidification to increase the bacteria count in the mixture. The mixture is then air dried slowly, e.g., for about 3–11 days under non-aseptic conditions, so that the moisture level in the bacteria is gradually reduced to less than 10%, preferably less than 5%, to form the inoculant composition. Drying at a relative humidity in the range of 35%–60% optimizes bacterial survival during desiccation. A final moisture level of about 5% or less is important for maximizing storage life.

The dried product is then milled using conventional equipment to a final particle size of 0.1 to 150 microns. The dry, dormant microorganism is then ready for coating, but may be shipped or stored in the interim, or may be premixed with the survival enhancing additive as discussed further below. As described above with reference to prior art processes, the dry, dormant microorganism formulated in a powder carrier, such as a clay, may be applied to seed as a dry application to the seed surface. This method of preinoculation provides very good microbial longevity on the seed in a dried state. However, inoculant application with a liquid seed-applied fungicide, such as Apron®, first requires the application of the fungicide, total drying of this treatment on the seed which normally requires greater than twelve hours, followed by the application of the dry inoculant. This multiple step process is time consuming and also generates dust from the dry inoculant. The present invention allows preparation of an inoculant, with or without a liquid fungicide, in a one-step efficient system without the generation of excessive dust. The present invention does not require that the bacteria be prepared at the same site at which the seeds will be coated.

The dry, dormant microorganisms are then mixed with an aqueous solution containing the carbohydrate in an amount effective to minimize the loss of viable cells during the subsequent drying process. The carbohydrate concentration in the solution should be about 0.5 to 75% weight carbohydrate to total volume of the solution (w/v) or v/v, preferably 20–50% w/v or v/v, depending upon the specific carbohydrate compound. Too low a concentration would not provide superior microbial survival on seed, whereas too high a concentration would result in a physical limitation, i.e., excessive slurry thickness or a slurry viscosity too high for seed application. For gum arabic, a 10%–50% w/v range is preferred, whereas for sucrose a somewhat higher range of 25%–75% provides the greatest improvement.

The aqueous mixture or slurry may then be coated onto the selected seeds by different coating processes. Film coating is a known process in which the coating mixture is sprayed onto the seeds, and the seeds are then passed rapidly into a drying zone where the water is driven off to leave a behind a film including a polymer, plasticizer and a pigment that colors the seeds. The seeds pass through several spraying and drying cycles in a fluidized bed or rotating drum so that successive layers of film coating build up to a desired thickness. The overall weight gain of the seed following film coating is preferably less than 10 wt. %, preferably about 3% or less in order to provide a higher count per unit weight.

A slurry method of coating the seeds utilizes a moist microbial inoculant combined with water or water plus fungicide to form an inoculant slurry which is mixed with seed and allowed to dry before bagging and distributing to end-users. Stickers may be incorporated to help retain the inoculant on the seed. This slurry method may be modified with the addition of lime ($CaCO_3$), polymers and other plant nutrients to form a pelleted or coated seed. This process adds the components as a slurry to the seed and dries these components on the seed. Pelleted seed may obtain seed weight gain from 10 to 50%.

Coating systems presently available commercially are well suited for use in the present invention because the total period of exposure to water can be minimized, e.g., kept to about 30–60 minutes. Periods of exposure to moisture up to about 3 hours are optimum, although it is possible for the exposure period to be as high as about 12 hours, though with diminished results. At 16 hours of exposure time, the carbohydrate becomes ineffective in providing superior survival upon drying of seed.

The amount of the microorganism-carrier composition added to the carbohydrate solution is preferably in the range of 1 to 30% w/v, especially 5–30% w/v (e.g., 20% w/v equals 20 g solid in 80 ml liquid.) Above 30% the mixture becomes excessively thick, whereas below 1% the amount of available microorganisms becomes small. The rate at which the resulting composition is added to the seeds is not critical and will vary depending on the desired bacteria count, the surface area of the seeds, and other factors. Values ranging from about 6 to 19 ml/lb proved useful in the examples below.

As illustrated by Example 4 below, initial attempts to prepare coated seeds using pre-dried bacteria and water as the additive resulted in a very poor survival rate when the coated seeds were rehydrated for use. Upon exposure to moisture, most of the previously dried, dormant bacteria lost their ability to survive in a dry state after coating. The effect becomes more severe the longer the pre-dried, dormant bacteria are exposed to water during the seed coating process. Thus, as discussed below, the coating step of the invention is carried out as rapidly as possible for best results. The moisture level of the microorganisms following seed coating has not been measured, but is most preferably not substantially higher than its former level, that is, less the 10 wt. % water, preferably less than 5 wt. % water. Known processes, such as those illustrated in the drawing, do not use a step of re-drying the microorganisms prior to rehydration in the soil.

Once coated and redried, the seeds may then be stored for prolonged periods before use. Prolonged exposure to moisture following planting causes the microorganisms coated on the seeds to rehydrate and begin to multiply in soil and interact with the emerging plant root. An alternate coated seed according to the invention is coated with both an inoculant bacteria and a biocidal bacteria which have each been previously dried to a dormant state prior to film coating.

The composition used to coat the seeds has a strong effect on the viability of the bacteria coated on the seeds. The carbohydrate compounds useful for enhancing survival after temporary rehydration according to the invention include gums, sugars, starches, and celluloses, particularly gum arabic, xanthan gum, sucrose, mannitol, maltose, trehalose, dextrin, dextran, and carboxymethylcellulose. These compounds are advantageous compared to non-carbohydrate compounds or additives such as mineral or other oils, polyethylene glycol (PEG), polyvinylpyrrolidone (PVP), and the like. Oils have been previously used to improve microbial survival in fertilizers, but leave the seeds with a sticky, oily film that provides unacceptable handling characteristics. Polymers such as PVP, which are acceptable as seed coating adhesion promoting agents (or stickers) did not significantly improve survival when used in the described method. Among the carbohydrates tested, sugar (sucrose) performed well. Natural gums, which are complex polysaccharides, especially gum arabic, provided unusually good results in the experiments described below and are most preferred for use in preparing coated seeds according to the invention.

The seeds to be coated according to the invention may be seeds from any plant species that can benefit from the presence of an inoculant or a plant-growth-promoting or pesticidal microbe. Most preferred are seeds of the well-known leguminous plants including soybeans, clovers, alfalfa, sweetclovers, peas, vetches, garden variety beans, and lupines. The inoculant bacterial species is selected to match.

The survival enhancing additive according to the invention may be added to the dry, dormant microorganisms prior to the coating step. The resulting composition according to the invention is then ready to ship to the coater without the need to add additional ingredients at the time of coating. Where the dry, dormant microorganisms are made by a slow drying process as described above, a carrier such as clay is usually incorporated into the composition along with the dry, dormant microorganisms and the survival enhancing additive. If the microorganisms have been freeze-dried, the carrier may be omitted.

One composition of the invention for use in coating seeds thus comprises the dry, dormant microorganisms, an effective amount of an additive such as a carbohydrate for enhancing survival of such microorganisms after exposure to water used in a coating step followed by drying of the coated seeds, and optionally a particulate carrier such as clay. If the carbohydrate is gum arabic, the amount of the gum arabic is preferably in the range of from about 25 to 70 wt. % of the amount of the total of the carbohydrate, the carrier and the dry, dormant microorganisms. If the carbohydrate is a sugar, the amount of the sugar is preferably in the range of from about 50 to 75 wt. % of the amount of the total of the carbohydrate, the carrier and the dry, dormant microorganisms. At a level of around $10^9$ viable bacteria per gram of the composition, the amount by weight of the microorganisms is small relative to the amount of the carrier particles.

An alternate composition of the invention for use in coating seeds is made of freeze-dried, dormant microorganisms and an effective amount of an additive such as a carbohydrate for enhancing survival of such microorganisms after exposure to water used in the coating process followed by drying of the coated seeds, wherein the composition is free of a particulate carrier. If the carbohydrate is gum arabic, the amount of the gum arabic is preferably in the range is at least about 98 wt. %, especially 98.0 wt. % to 99.6 wt. % of the total of the carbohydrate and the dry, dormant microorganisms. If the carbohydrate is a sugar, the amount of the sugar is preferably at least about 99 wt. % of the total of the carbohydrate and the dry, dormant microorganisms, particularly 99.2 to 99.7 wt. %, relative to the microorganisms.

In the examples which follow, a dry microbial preparation was added to an aqueous additive solution containing one of a number of different carbohydrate compounds of specific concentration. The slurry preparation was then applied to seeds and subsequently dried down on the seeds with a total period of exposure to water of about 1.5 hours. Determination of microbial population on the seeds was accomplished using a standard dilution plating procedure. Specific microorganism population size will differ depending on a number of factors, including the specific microbe, carbohydrate utilized, and seed type.

EXAMPLE 1

This example describes an experiment in which a number of different organic compounds were evaluated for their effect on survival of *Rhizobium meliloti* in a slurry preparation, and when the slurry was dried down on seed. The *R. meliloti* bacteria used for this experiment were in a dry (≦5% moisture), clay-based preparation at a concentration of 6.5×10⁸ cfu/g. The organic compounds tested are listed in Table 1. Those compounds in liquid form were evaluated as is, while those in powder form were added to water at differing concentration, depending upon the product (Table 1). The dry *R. meliloti* preparation was added to each organic additive at a rate of 20% w/v, and mixed with a spatula until the slurry was uniform. The slurry was allowed to incubate at room temperature (78–82° F.) for one hour, then dilution plated for viable cell count (see Table 1.)

To assess the performance of each additive or additive concentration in maintaining *R. meliloti* survival, the results are also expressed in terms of the percent of theoretical count. The theoretical count is determined based on the known number of rhizobia added to the additive and the slurry volume. Gum arabic and sucrose yielded the highest per cent of theoretical count, with gum arabic being uniform across the concentrations tested, and sucrose increasing with concentration.

The above-mentioned *R. meliloti*/organic additive slurries were applied to alfalfa seed at a rate of 6.3 ml/lb of seed. The slurries were applied to seed by shaking in a plastic bag until the seeds were uniformly coated. The seeds were dried for 30 minutes, then assayed by dilution plating for cfu/seed. A comparative treatment was prepared by application of an equivalent amount of the dry *R. meliloti* preparation to seed (1.26 g/lb seed). In this and the other examples which follow, each application provided the same number of viable organisms per seed.

The seed treatment results are presented in Table 2. As with the slurry counts, gum arabic and sucrose provided the highest seed counts. Counts increased with concentration with sucrose and one of the gum arabic products, with counts at the highest concentration tested being in excess of the dry *R. meliloti* sample. Seed counts were more consistent across concentration with the second gum arabic product, with the count being in excess of the dry sample at all of the concentrations tested. Seed counts were not obtained with some of the non-carbohydrate compounds due to failure of the resultant slurries to dry down on seed, instead producing an oily appearance.

TABLE 1

| Additive | Additive concentration (w/v) | cfu/ml of slurry | Percent of theoretical count[1] |
|---|---|---|---|
| Gum arabic (1)[2] | 5% | 3.3 × 10⁷ | 25.4 |
| | 10% | 3.1 × 10⁷ | 23.8 |
| | 20% | 3.1 × 10⁷ | 23.8 |
| Gum arabic (2)[2] | 5% | 2.6 × 10⁷ | 20.0 |
| | 10% | 3.0 × 10⁷ | 23.1 |
| | 20% | 3.2 × 10⁷ | 24.6 |
| PVP K-15 | 5% | 6.7 × 10⁶ | 5.2 |
| | 10% | 4.2 × 10⁶ | 3.2 |
| | 20% | 2.1 × 10⁶ | 1.6 |
| Sucrose | 10% | 2.2 × 10⁷ | 16.9 |
| | 25% | 3.8 × 10⁷ | 29.2 |
| | 50% | 5.0 × 10⁷ | 38.5 |
| Arabino-galactan | 5% | 9.1 × 10⁶ | 7.0 |
| | 10% | 6.7 × 10⁶ | 5.2 |
| | 20% | 6.5 × 10⁶ | 5.0 |
| Methyl-cellulose | 1% | 7.1 × 10⁶ | 5.5 |
| PEG 400 | — | 1.55 × 10⁷ | 11.9 |
| Propylene glycol | — | 5.0 × 10⁶ | 3.8 |
| Mineral oil | — | 9.7 × 10⁶ | 7.5 |

[1]Theoretical count of dry *Rhizobium meliloti* preparation: 1.3 × 10⁸ cfu/ml
[2]Obtained from alternate suppliers

TABLE 2

| Additive | Additive concentration (w/v) | cfu/seed |
|---|---|---|
| None[1] | — | 86 |
| Gum arabic (1)[2] | 5% | 150 |
| | 10% | 331 |
| | 20% | 306 |
| Gum arabic (2)[2] | 5% | 59 |
| | 10% | 66 |
| | 20% | 414 |
| PVP K-15 | 5% | 18 |
| | 10% | 30 |
| | 20% | 80 |
| Sucrose | 10% | 11 |
| | 25% | 84 |
| | 50% | 364 |
| Arabinogalactan | 5% | 5 |
| | 10% | 18 |
| | 20% | 177 |
| Methylcellulose | 1% | 50 |

[1]*Rhizobium meliloti* preparation applied dry to seed at a rate equivalent to the slurry treatments (1.26 g/lb seed)
[2]Obtained from alternate suppliers

EXAMPLE 2

This example describes an experiment further evaluating the effect of gum arabic on survival of *Rhizobium meliloti* in a slurry application on seed. As in Example 1, the *R. meliloti* bacteria used for this experiment were in a dry (≦5% moisture), clay-based preparation at a concentration of 6.5× 10⁸ cfu/g. Aqueous suspensions of gum arabic were prepared in increments of 5% from 20 to 40% w/v. The dry *R. meliloti* preparation was added to each solution of gum arabic at a rate of 20% w/v, and mixed with a spatula until the slurry was uniform. The slurries were allowed to incubate at room temperature (78–82° F.) for one hour, then applied to alfalfa seed at a rate of 6.3 ml/lb of seed. The slurries were applied to seed by shaking in a plastic bag until the seeds were uniformly coated. The seeds were dried for 30 minutes, then assayed by dilution plating for cfu/seed.

As in Example 1, a comparative treatment was prepared by application of an equivalent amount of the dry *R. meliloti* preparation to seed (1.26 g/lb seed). The seed treatment results are presented in Table 3. Seed counts were high across all concentrations of gum arabic, ranging from 586 to 805 cfu/seed compared to only 86 cfu/seed with the dry *R. meliloti* comparison. With the exception of the count obtained at 30% concentration, counts increased with increasing concentration of gum arabic.

TABLE 3

| Additive | Additive concentration (w/v) | cfu/seed |
|---|---|---|
| None[1] | — | 86 |
| Gum arabic | 20% | 616 |
| | 25% | 623 |
| | 30% | 586 |
| | 35% | 675 |
| | 40% | 805 |

[1]*Rhizobium meliloti* preparation applied dry to seed at equivalent rate to slurry treatments (1.26 g/lb seed)

EXAMPLE 3

The effect of gum arabic on survival of *Rhizobium meliloti* in a slurry application on seed was evaluated when application was carried out by a commercial film coating process. The R. meliloti bacteria used in this experiment were in a dry ($\leq 5\%$ moisture), clay-based preparation similar to that utilized in Examples 1 and 2, but had a concentration of $7.4 \times 10^8$ cfu/g. Film coating solutions were prepared containing gum arabic at a concentration of 20, 30, and 40% w/v. The dry R. meliloti preparation was added to each solution at a rate of 20% w/v, and mixed for a period of 10 minutes before application on seed.

The slurries were applied to alfalfa seed using a spray gun at a rate of 18.9 ml/lb of seed in a lab scale conventional coating pan. Indirect air was applied to aid in the drying process and the temperature was kept below 80° F. As in the prior examples, a comparative treatment was prepared by application of an equivalent amount of the dry R. meliloti preparation to seed (3.78 g/lb seed). The resultant seed treatments were assayed by dilution plating for cfu/seed. The results are presented in Table 4. The film coated seed treatment counts were similar across the three gum arabic concentrations tested, averaging ~1,600 cfu/seed.

TABLE 4

| Additive | Additive concentration (w/v) | cfu/seed |
|---|---|---|
| None[1] | — | 4,614 |
| Gum arabic | 20% | 1,614 |
| | 30% | 1,659 |
| | 40% | 1,545 |

[1]Rhizobium meliloti preparation applied dry to seed at equivalent rate to slurry treatments (3.78 g/lb seed)

The R. meliloti strain used in this example and Examples 4 and 5 below was a different one from that used in Examples 1 and 2. As shown in Table 3, the invention makes it possible to use a wider range of inoculant strains with greater viability.

EXAMPLE 4

This example describes an experiment further evaluating the effect of two gum arabic products, obtained from alternate sources, on survival of Rhizobium meliloti in a slurry application on seed. The R. meliloti bacteria used in this experiment were in a dry ($\leq 5\%$ moisture), clay-based preparation similar to that utilized in Examples 1 and 2, but had a concentration of $7.4 \times 10^8$ cfu/g. Aqueous suspensions of the gum arabic products were prepared at concentrations of 20 and 40% w/v. The dry R. meliloti preparation was added to each solution of gum arabic at a rate of 20% w/v, and mixed with a spatula until the slurry was uniform. The slurries were allowed to incubate at room temperature (78–82° F.) for one hour, then applied to alfalfa seed at a rate of 6.3 ml/lb of seed. The slurries were applied to seed by shaking in a plastic bag until the seeds were uniformly coated. The seeds were dried for 30 minutes, then assayed by dilution plating for cfu/seed.

A control seed treatment was included. The negative control was prepared as stated above, except that water alone was used as the additive for the dry R. meliloti preparation. As in other examples, a comparative treatment with no additive was prepared by application of an equivalent amount of the dry R. meliloti preparation to seed (1.26 g/lb seed).

The seed treatment results are presented in Table 5. The control and comparative treatments illustrate the strong negative effect that exposure to water has on the previously dehydrated inoculant. Both concentrations of the two gum arabic products dramatically improved seed count compared to the water control, and provided seed counts 16.6–66.6% greater than that observed with the dry sample.

TABLE 5

| Additive | Additive concentration (w/v) | cfu/seed |
|---|---|---|
| None[1] | — | 955 |
| Water | — | 36 |
| Gum arabic[2] | 20% | 1,318 |
| | 40% | 1,114 |
| Gum arabic[2] | 20% | 1,523 |
| | 40% | 1,591 |

[1]Rhizobium melilote preparation applied dry to seed at equivalent rate to slurry treatments (1.26 g/lb seed).
[2]Obtained from alternate suppliers.

The foregoing results illustrate that addition of a carbohydrate, especially a gum such as gum arabic, to the coating mixture results in a greater count of viable bacteria after the coating process has been completed. A count of 1,000 cfu/seed is a well known standard for acceptability.

EXAMPLE 5

This example compares two alternate methods of slurry preparation for effect on R. meliloti survival on seed. The R. meliloti bacteria used in this example were in the same dry ($\leq 5\%$) clay-based preparation with a count of $7.4 \times 10^8$ cfu/g used in Examples 3 and 4. The first method of slurry preparation was that described in prior examples, i.e., preparation of an aqueous gum arabic solution, followed by addition of the dry R. meliloti preparation. The second method of slurry preparation was done by pre-blending the dry R. meliloti preparation and gum arabic powder, followed by addition of water. In each case, the R. meliloti preparation and gum arabic slurry concentrations were 20% and 16% w/v, respectively. The slurries were allowed to incubate at room temperature (78–82° F.) for one hour, then applied to alfalfa seed at a rate of 6.3 ml/lb of seed. The slurries were applied to seed by shaking in a plastic bag until the seeds were uniformly coated. The seeds were dried for 30 minutes, then assayed by dilution plating for cfu/seed. As in other examples, a comparative treatment with no additive was prepared by application of an equivalent amount of the dry R. meliloti preparation to seed (1.26 g/lb seed).

The seed treatment results are presented in Table 6. Both of the gum arabic slurry treatments improved seed count relative to the dry R. meliloti comparison treatment.

TABLE 6

| Additive | Means of slurry preparation | R. meliloti prep./gum arabic slurry conc. (%) | cfu/ seed | Change vs. no additive control (%) |
|---|---|---|---|---|
| None[1] | — | — | 955 | — |
| Gum arabic | (Gum arabic + water) + R. meliloti preparation | 20/16 | 1,523 | +59.5 |
| Gum arabic | (Gum arabic + R. meliloti preparation) + water | 20/16 | 1,227 | +28.5 |

[1]Rhizobium meliloti preparation applied dry to seed at a rate equivalent to the slurry treatments (1.26 g/lb seed).

It will be understood that the foregoing description is of preferred exemplary embodiments of the invention, and that the invention is not limited to the specific forms shown.

Modifications may be made without departing from the scope of the invention as expressed in the appended claims.

We claim:

1. A process for coating seeds, comprising:

coating seeds with a coating composition comprising dried, dormant microorganisms, water, and an additive which comprises a carbohydrate and which is effective for enhancing survival of the microorganisms during exposure to the water used in the coating step; and then drying the coated seeds to produce seeds coated with a film containing dry, dormant microorganisms;

wherein the coating and drying steps are conducted so that the dried, dormant microorganisms become moistened for a sufficient time to form the coated seeds and are returned to a dry state within a total water exposure period of no more than about 12 hours.

2. The process of claim 1, wherein the microorganisms comprise rhizobia or bradyrhizobia of a species and in an amount effective to promote nitrogen fixation in a plant growing from the coated seed.

3. The process of claim 2, wherein the microorganisms are of a strain selected form the group consisting of *R. meliloti, R. leguminosarum* biovar *trifolii, R. leguminosarum* biovar *viceae, R. leguminosarum* biovar *phaseoli,* and *B. japonicum.*

4. The process of claim 2, wherein the microorganisms comprise a strain of *R. meliloti* and the seeds are alfalfa seeds.

5. The process of claim 1, wherein the microorganisms comprise biocidal bacteria in an amount effective to reduce disease infestation by a target pest of a plant growing from the coated seed.

6. The process of claim 2, wherein the microorganisms further comprise a biocidal bacteria in an amount effective to reduce disease infestation by a target pest of a plant growing from the coated seed.

7. The process of claim 5, wherein the biocidal bacteria are of a strain selected from the group consisting of *Pseudomonas putida* and *Bacillus cereus.*

8. The process of claim 5, wherein the microorganisms further comprise a biocidal bacteria comprising ATCC 53522 in an amount effective for control of damping off and root rot of plants germinating from the coated seeds.

9. The process of claim 1, wherein the film forming composition further comprises an effective amount of a particulate carrier.

10. The process of claim 9, wherein the particulate carrier consists essentially of clay.

11. The process of claim 10, wherein said dried, dormant microorganisms are produced by a process which comprises:

culturing the microorganisms in a growth medium to form a culture;

mixing the culture containing the microorganisms with an inert powdered clay carrier;

incubating the culture-carrier mixture for at least about 1 day under conditions effective to increase the microorganisms count in said mixture; and drying the resulting mixture so that the moisture level in said microorganisms is gradually reduced to less than about 5 wt. % to form the dried, dormant microorganisms.

12. The process of claim 1, wherein the total water exposure period is about 3 hours or less.

13. The process of claim 1, wherein the carbohydrate is selected from the group consisting of gums, sugars, starches, celluloses, and combinations thereof.

14. The process of claim 1, wherein the carbohydrate consists essentially of gum arabic.

15. The process of claim 11, wherein said coating composition is formed by mixing a carbohydrate solution with said dried, dormant microorganisms.

16. A process for coating seeds, comprising:

coating seeds with a film-forming composition comprising dried, dormant bacteria comprising rhizobia or bradyrhizobia of a species and in an amount effective to promote nitrogen fixation in a plant growing from the coated seed, a particulate carrier, water, and an amount of a carbohydrate effective for enhancing survival of the bacteria during exposure to the water; wherein said composition is formed by admixing a solid mixture of said dried, dormant microorganisms and said particulate carrier with a solution comprising water and said carbohydrate; and then drying the coated seeds, to form seeds coated with a film containing dry, dormant microorganisms;

wherein the admixing, film coating and drying steps are conducted so that the dry, dormant bacteria become moistened for a sufficient time to form the film-coated seeds and are returned to a dry state within a total water exposure period of not more than about 12 hours.

17. Seeds coated according to the process of any one of claims 1–16.

* * * * *